United States Patent [19]

Perego et al.

[11] Patent Number: 5,041,094

[45] Date of Patent: Aug. 20, 1991

[54] DEVICE FOR ADMINISTERING FLUID DRUGS, IN PARTICULAR FOR INFUSION

[75] Inventors: Jean Perego, Longvic; Francois B. Perego, Tinténiac; Patrick Guyondet, Brosey sur Tille, all of France

[73] Assignee: Societe de Produits pour l'Industrie la Recherche et les Analyses de Laboratoires (S.P.I.R.A.L.) Société à responsabilité limitée dite, Arc-sur-tille, France

[21] Appl. No.: 350,588

[22] PCT Filed: Jul. 25, 1988

[86] PCT No.: PCT/FR88/00386

§ 371 Date: May 22, 1989

§ 102(e) Date: May 22, 1989

[87] PCT Pub. No.: WO89/00866

PCT Pub. Date: Feb. 9, 1989

[30] Foreign Application Priority Data

Jul. 31, 1987 [FR] France ................ 87 10881

[51] Int. Cl.$^5$ ................ A63M 37/00; G01F 11/00
[52] U.S. Cl. ................ 604/143; 604/131; 604/148; 128/DIG. 12; 222/389
[58] Field of Search ................ 604/49, 51, 52, 141, 604/150, 131, 118, 890.1, 143; 222/389, 386, 326, 327, 183, 212; 128/DIG. 12

[56] References Cited

U.S. PATENT DOCUMENTS

| | | | |
|---|---|---|---|
| 4,201,207 | 5/1980 | Buckles et al. | 128/214 F |
| 4,298,000 | 11/1981 | Thill et al. | 128/218 A |
| 4,346,703 | 8/1982 | Dennehey et al. | 128/213 A |
| 4,561,856 | 12/1985 | Cochran | 604/143 |
| 4,685,596 | 8/1987 | Mattheis | 604/143 |
| 4,744,786 | 5/1988 | Hooven | 604/143 |
| 4,773,900 | 9/1988 | Cochran | 604/143 |
| 4,915,693 | 4/1990 | Hessel | 128/DIG. 12 |

FOREIGN PATENT DOCUMENTS

| | | |
|---|---|---|
| 2447198 | 3/1984 | France . |
| 2447199 | 5/1984 | France . |
| 2499857 | 11/1985 | France . |
| 2040379A | 8/1980 | United Kingdom . |
| 2063684A | 6/1981 | United Kingdom . |

OTHER PUBLICATIONS

"Le Monde", No. 13135, dated Apr. 22, 1987, and published on Apr. 21, 1987.
"Le Quotidien du Pharmacien", No. 779, Jan. 11, 1989.

Primary Examiner—Richard J. Apley
Assistant Examiner—Karen G. Horowitz
Attorney, Agent, or Firm—Foley & Lardner

[57] ABSTRACT

The invention concerns a device and a process for administering a liquid drug preparation, in particular by infusion, by implantation or percutaneously, at a given flow rate for relatively long period of time, using a technique involving the retractation of an elastic membrane. More specifically, using this technique, said drug preparation is placed in a tubular reservoir (13) where it is subjected to the action of at least one movable wall (112, 112a). The movable wall is displaced by the pressure of a hydraulic fluid (10), the entry of which is controlled by a capillary tube (4) fed with hydraulic fluid (10) under pressure by a hydraulic accumulator subject to the thrust of a previously dilated retractable elastic membrane (8).

18 Claims, 2 Drawing Sheets

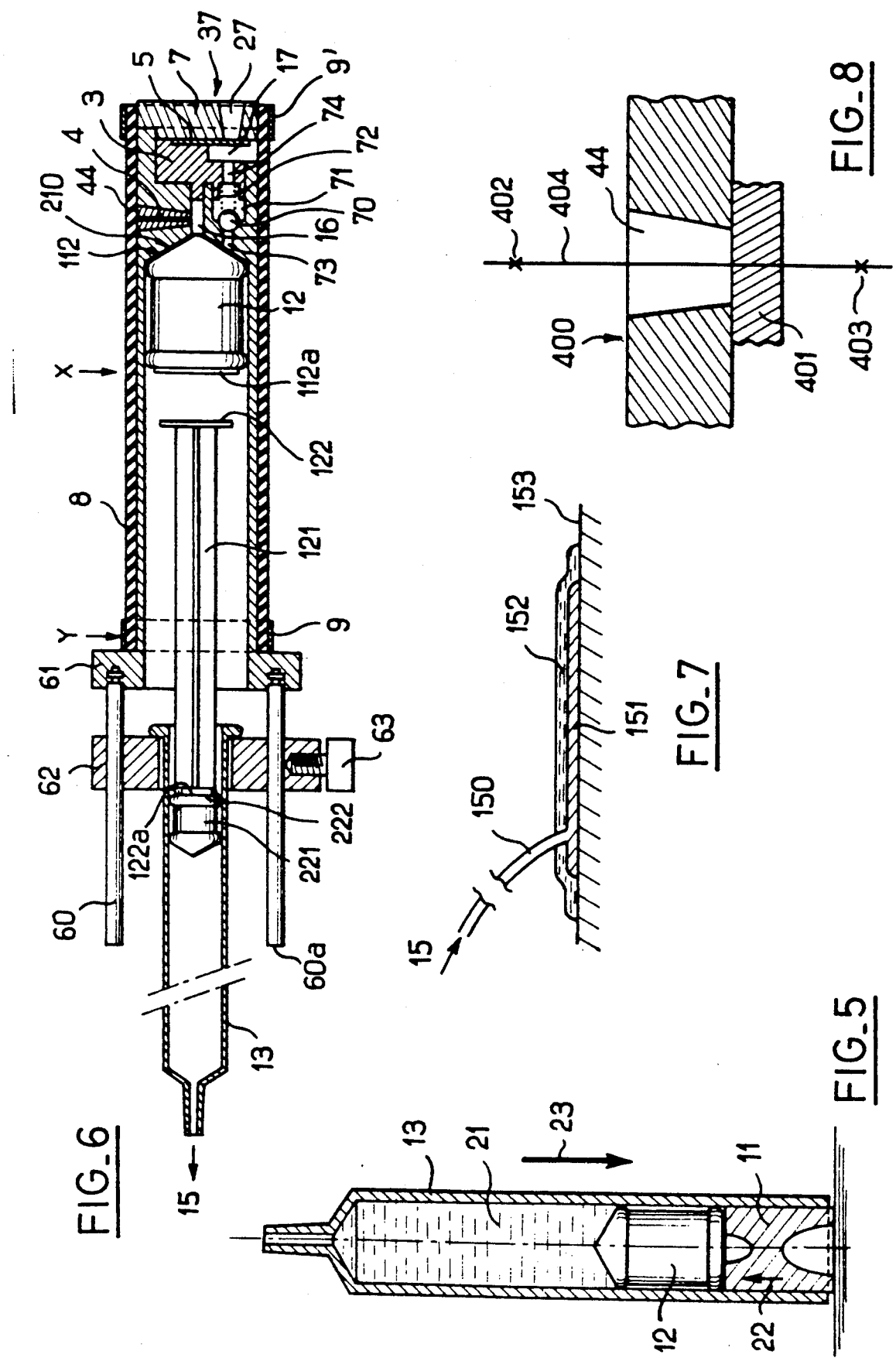

DEVICE FOR ADMINISTERING FLUID DRUGS, IN PARTICULAR FOR INFUSION

BACKGROUND OF THE INVENTION

1. Field of the Invention

The present invention relates to the field of the administration of a medicinal preparation, preferably (i) in a relatively small amount and (ii) for relatively long periods of time.

More precisely, it relates to an administration method and device which can be used mainly in the field of arterial, venous or subcutaneous perfusion and also in the field of the percutaneous administration of active principles, where the said active principles, placed in contact with the skin, pass through the skin and enter the organism.

By virtue of this method and this device, the strictly necessary amount of medicinal preparation is administered to the patient, especially by perfusion.

2. DESCRIPTION OF THE RELATED ART

It is known that two apparatuses have hitherto been used for perfusion in hospitals, namely the drip and the automatic syringe.

The drip, which is often used because it is very economic, gives a very random flow, it being possible for the volume of perfusion liquid administered to vary by ±150% since it is adjusted manually. The drip has several other disadvantages, i.e. especially (i) the introduction of a large volume of liquid (generally isotonic) into the patient's systemic circulation, which is not always desirable, in particular if the patient is suffering from renal or other disorders which prevent or limit urination, and (ii) immobilazation of the patient.

On the other hand, the automatic syringe, when it is actually working, is theoretically very efficient as regards the precision of the flow; it delivers a uniform flow and only introduces the strictly required amount of perfusion liquid into the systemic circulation. Unfortunately, the automatic syringe has numerous disadvantages: it involves immobilizing the patient, is relatively very expensive, frequently breaks down and requires highly qualified technical staff to make the required flow adjustments (not always easy).

It is also known that, as far as the drip technique is concerned, devices for the continuous perfusion of ambulant patients have been proposed. French patent documents 2,447,198, 2,447,199 and 2,499,857, in particular, have disclosed a device comprising a pliable and flexible container of solution, a transfer orifice connected to the said container and a flexible tube running from the said orifice to the patient's catheter, which is provided with a breakable element.

U.S. Pat. No. 4,298,000 has disclosed a perfusion device in which a capillary for regulating the flow of the medicinal preparation to be administered is located downstream of the reservoir containing the said preparation.

The said document neither describes nor suggests the use, upstream of the said reservoir, of (i) a hydraulic accumulator of the type comprising a flexible membrane fixed in a leaktight manner around the said device, or (ii) a capillary regulating the admission of the hydraulic fluid for pushing the perfusion preparation towards its administration site.

Also, U.S. Pat. No. 4,201,207 has disclosed another perfusion device, in which the preparation to be administered is accommodated in a rubber envelope (or bladder), which is compressed and discharges into a distributing element via a capillary needle. The said document neither describes nor suggests the use of a hydraulic accumulator acting upstream of the reservoir containing the perfusion preparation, via a capillary regulating the admission of the hydraulic fluid driving a piston for pushing the said preparation towards its administration site.

Finally, the daily newspaper "Le Monde" of Wednesday 22 Apr. 1987 (published on 21 Apr. 1987) disclosed, on page 23, that a perfusion device for chemotherapeutic chemotherapeutic treatment had been recommended. The said device, the principle of which is based on the retraction of a latex membrane, comprises a large syringe equipped with a balloon-shaped reservoir of 70 ml capacity, and a flow controller apparently provided with a filter membrane of 5 μm mesh. Via the said filter membrane, the said device delivers 2 ml/h of medicinal solution for venous, arterial or subcutaneous administration by means of a catheter. Now, the retraction of a latex membrane alone does not ensure uniformity of the flow of the medicinal preparation to be distributed.

SUMMARY OF THE INVENTION

In the field of perfusion, there is a need for equipment which is simple to use, efficient and inexpensive and by means of which the amount of liquid to be administered can be limited to the strict minimum.

According to the invention, a novel technical solution is proposed which is suitable for arterial, venous or subcutaneous perfusion as well as percutaneous administration, which is also known as transcutaneous administration. This novel technical solution has the advantages of the automatic syringe in terms of the uniformity of flow and the strict volume of medicinal preparation to be administered, and the advantages of the drip in terms of the economic aspect, without the abovementioned disadvantages of the said automatic syringe and drip.

Like the perfusion device described in "Le Monde", this novel technical solution is based on the retraction of an elastic membrane, but it differs therefrom in the use of different means, especially the presence of a capillary duct in the hydraulic system, restraining the circulation of the hydraulic fluid. The flow of the medicinal preparation to be administered according to the invention is regulated in the hydraulic system by the capillary and the viscosity of the hydraulic fluid acting as the working or driving fluid.

This novel technical solution has the advantage that it can be applied to both hospitalized patients and ambulant patients. In particular, it makes it possible to carry out perfusions continously at very low flow rates, for example of less than 1 ml per 24 h, in particular flow rates of the order of 1 ml/72 h, and even to obtain flow rates of the order of 10 ml/year, or 5 to 1 ml/year if necessary, in the case of a device implanted in the organism. Such low flow rates greatly reduce the toxicity of the active principles, which were often administered in the past by massive and successive injections.

Thus, according to the invention, a method is recommended for the administration of a liquid medicinal preparation, especially by perfusion, by implantation or percutaneously, at a determined rate for a relatively long period of time,. The method comprises providing a device for the continuous administration of a liquid medicinal preparation with a body having a reservoir disposed in the body and an elastic membrane surrounding at least a portion of the body; dilating an elastic membrane by inserting fluid into the membrane, placing a medicinal preparation in a reservoir and forcing the fluid into one moving wall by refracting the elastic membrane to administer the medicinal preparation from the reservoir. The hydraulic fluid admission is controlled by a capillary duct supplied with hydraulic fluid under pressure by a hydraulic accumulator driven by a retractable elastic membrane dilated beforehand, the said reservoir being housed in a longitudinal recess leading to the outside and hollowed out of a cylindrical body, the said elastic membrane being fixed in a leaktight manner to at least a portion of the outer surface of the said cylindrical body, the said hydraulic accumulator comprising a hydraulic fluid which can be accommodated in the space situated between (a) the said elastic membrane dilated by the said fluid, and (b) the said portion of outer surface of the said cylindrical body which is covered by the said elastic membrane.

According to the invention, a device for the continuous administration of a liquid medicinal preparation, especially by perfusion, by implantation or percutaneously, is also recommended as a novel industrial product, the said device—which has a hydraulic system and a reservoir and in which the hydraulic fluid circulated by the retraction of an elastic membrane dilated beforehand ensures, via a piston, continuous distribution of the said preparation, contained in the said reservoir, towards its administration site—comprising, in the said hydraulic system, a hydraulic accumulator driven by a retractable elastic membrane, a capillary duct supplied with hydraulic fluid by the said hydraulic accumulator, and a piston located downstream of the said capillary duct and driven by the hydraulic fluid coming from the said capillary duct, the said piston being intended for continuous transfer of the medicinal preparation, contained in the said reservoir, towards the said administration site, the said reservoir being housed in a longitudinal recess leading to the outside and hollowed out of a cylindrical body, the said elastic membrane being fixed in a leaktight manner to at least a portion of the outer surface of the said cylindrical body, the said hydraulic accumulator comprising a hydraulic fluid which can be accomodated in the space situated between (a) the said elastic membrane dilated by the said fluid, and (b) the said portion of outer surface of the said cylindrical body which is covered by the said elastic membrane.

The flow of the medicinal preparation administered is regulated by the diameter of the capillary duct and the viscosity of the hydraulic fluid. In practice, the internal diameter of the capillary duct will be within the range from 10 $\mu$m to 90 $\mu$m, and preferably between 30 $\mu$m and 80 $\mu$m, for a hydraulic fluid such as water or a water/ethylene glycol or water/propylene glycol mixture, and within the range from 100 to 900 $\mu$m for a hydraulic fluid of higher viscosity, such as silicone oil or jojoba oil. As will be seen later, it is important for the said diameter to be essentially constant over the entire length of the duct from its inlet to its outlet. For the purpose of standardizing industrial production, it will be advantageous to use capillary ducts whose diameters and heights are rigorously fixed for the administration of a given volume of medicinal preparation over a given period of time.

In practice, the hydraulic fluid will be an essentially non-compressible liquid or a liquid of low compressibility. A liquid which is particularly suitable for this purpose is selected from the group consisting of water, saline aqueous solutions, oils (for example paraffin oil, palm oil, groundnut oil, linseed oil, olive oil, jojoba oil, etc.), alkylene glycols such as ethylene glycol and propylene glycol, polyalkylene glycols (such as polyethylene glycols and polypropylene glycols) (sic) which are liquid under normal temperature and pressure conditions), silicones and mixtures thereof. If appropriate, the hydraulic fluid may be gaseous, although liquid fluids are preferred to gaseous fluids. In general, according to the invention, the hydraulic fluid will never be in contact with the medicinal preparation to be administered.

According to the best way of putting the invention into effect, a device is recommended which comprises a cylindrical body out of which a longitudinal recess has been hollowed. The recess leads to the outside and its bottom has a channel through which hydraulic fluid can be supplied. The device also has an elastic membrane fixed in a leaktight manner to at least a portion of the outer surface of the cylindrical body. In addition a hydraulic accumulator is provided comprising a hydraulic fluid which can be accommodated in the space situated between the elastic membrane dilated by the hydraulic fluid, and the portion of outer surface of the cylindrical body which is covered by the said elastic membrane.

A capillary duct is also required which is intended on the one hand to be supplied with hydraulic fluid by the hydraulic accumulator, and on the other hand to supply the introduction channel which is located downstream of the capillary duct at the bottom of the recess in the said cylindrical body with hydraulic fluid. Additionally at least one piston is situated in the recess in the cylindrical body and it is capable of moving axially inside the recess. This piston comprises a first distal face driven directly by the hydraulic fluid coming from the fluid introduction channel, and a second distal face used for continuous distribution of the medicinal preparation towards its administration site.

Finally a tubular reservoir is provided to contain the liquid medicinal preparation to be administered. The reservoir and the hydraulic system being designed in such a way that the tubular reservoir is integral with the cylindrical body and associated with the piston.

Further advantages and characteristics of the invention will be understood more clearly from the following description of embodiments, which in no way imply a limitation but are given by way of illustration, in conjunction with the attached drawings, in which:

BRIEF DESCRIPTION OF THE DRAWINGS

FIGS. 4 and 5 schematically illustrate the modalities for prior manipulation of the reservoirs of the devices in FIGS. 1 and 3 before the said devices are brought into service;

FIG. 6 schematically illustrates the use of a device analogous to that in FIG. 1, designed as an automatic syringe;

FIG. 7 illustrates a percutaneous mode of administration by means of a device according to the invention; and FIG. 8 illustrates an embodiment of the capillary duct of the invention.

DETAILED DESCRIPTION OF THE PREFERRED EMBODIMENTS

Figure 1:
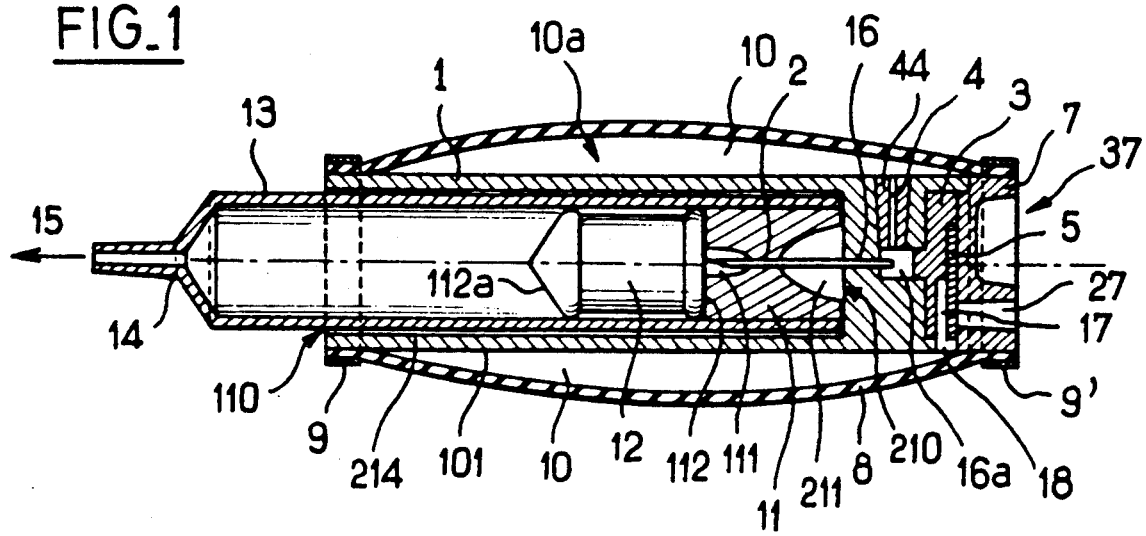
FIG. 1 is a cutaway view of a first device according to the invention.

The device according to the invention comprises (a) a tubular reservoir 13 containing the medicinal preparation to be administered (designated by 21 in FIG. 4), and (b) a hydraulic system having mainly a hydraulic accumulator 10 when the said device is brought into service for transfer of the medicinal preparation towards its administration site, an elastic membrane 8 acting continuously, during its retraction, on the hydraulic fluid 10 so as to ensure its circulation in the said hydraulic system, a hydraulic accumulator driven by the said membrane 8, a capillary duct 4 supplied with hydraulic fluid by the said accumulator, a piston 12 driven by the said hydraulic fluid coming from the said capillary duct 4, and at least one means, especially the feed tube 16, for directing the said hydraulic fluid, inside the cylindrical body 1, from the outlet of the capillary 4 towards the distal face 112 of the said piston 12.

The cylindrical body 1 performs a static function, namely the fixing of the reservoir 13, and a dynamic function, namely the cooperation of the hydraulic system with the said reservoir for continous transfer of the medicinal preparation towards its administration site, where the said preparation is introduced continuosly into the human body. In practice, it is designed so as to allow the hydraulic fluid to circulate from the hydraulic accumulator towards the piston 12.

The said cylindrical body 1 (see FIGS. 1, 2, 3 and 6) comprises a first longitudinal recess 110 leading to the outside, whose axis is parallel or identical to that of the said cylindrical body. The bottom of the recess 110 has a channel 16 for the introduction of hydraulic fluid so that the latter acts on the distal face 112 of the piston 12.

On the side opposite the first recess 110, the cylindrical body 1 has several other recesses: one recess for housing the capillary device 44 comprising the capillary duct 4, at least one recess for housing a system 37 for charging the hydraulic accumulator with hydraulic fluid, and, if appropriate, at least one recess for the recycling of the hydraulic fluid (see FIG. 6), after administration of the contents of the reservoir 13, so as to cause the said fluid to return to the hydraulic accumulator.

Figure 2:
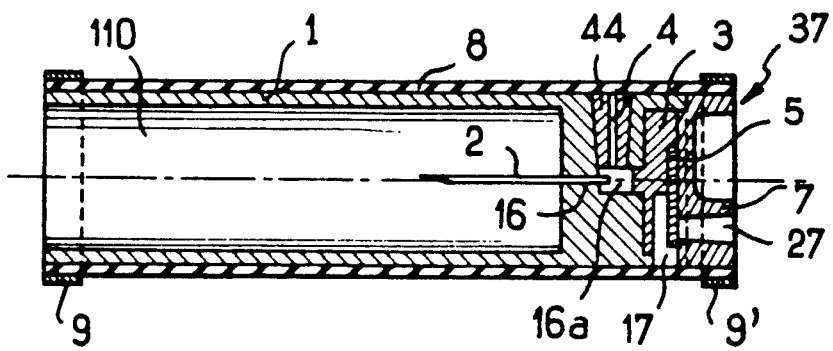
FIG. 2 is a cutaway view of the cylindrical body of the device in FIG. 1.

As shown in FIGS. 1, 2 and 6, the system 37 for charging or introducing the hydraulic fluid into the hydraulic system can be of the type comprising a part 7, which can be housed in the body 1 in the vicinity of the end of the recess opposite the recess 110. This part 7 is provided for example with a channel 27 for introduction of the hydraulic fluid, especially by injection with a syringe or any other appropriate device. The channel 27 can be blocked internally by a check valve 5 or an analogous means. A partition 3 is located in the body 1 behind the said part 7. This partition creates a separation between (i) the hydraulic fluid charging circuit, which comprises the internal cavity 17 situated in the space between the part 7, the valve 5 and the partition 3, on the one hand, and the slot 18 provided in the body 1 for supplying the space 10a in the hydraulic accumulator, on the other, and (ii) that portion of the circuit of the hydraulic system which comprises either the introduction channel 16 on its own (FIG. 6) or the said channel 16 together with the cavity 16a located between the outlet of the capillary duct 4 and the said channel 16 (FIGS. 1, 2 and 3).

The introduction of the hydraulic fluid via the system 37 in FIGS. 1, 2 and 6 is advantageously effected by means of a syringe without a needle, containing the said fluid. The tip of the syringe is introduced into the channel 27. The effect of this operation is to open the valve 5, which is generally made of rubber or other appropriate materials. Pushing the plunger of this syringe causes the said fluid which it contains to pass into the cavity 17 and then, via the slot 18 provided in the vicinity of the surface 101 of the cylindrical body 1, into the space 10a. The membrane 8 dilates as the space 10a fills up. If it is desired to stop administration of the medicinal preparation 21 contained in the tubular reservoir 13 before the said administration is complete, the tip of the empty syringe without a needle is introduced into the channel 27 and, under the pressure of the hydraulic accumulator, all the fluid 10 contained in the space 10a passes into the said syringe.

Figure 3:
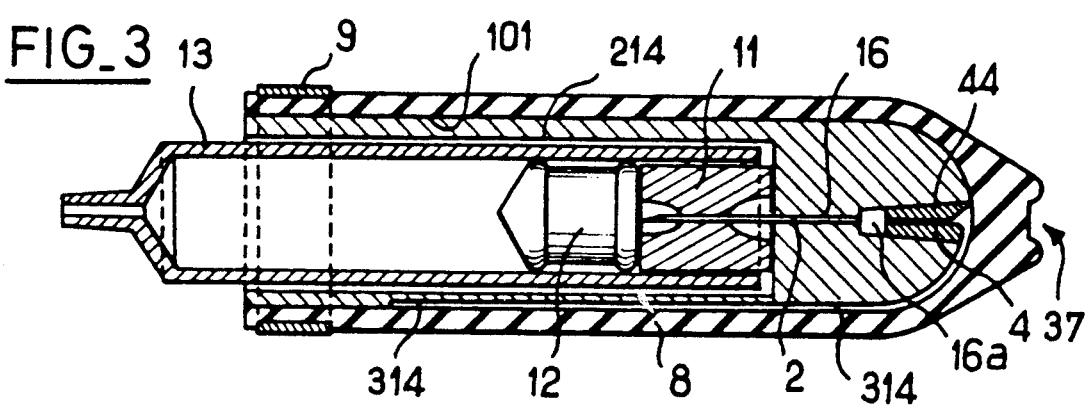
FIG. 3 is a schematic cutaway view of a second device according to the invention, which differs from that in FIG. 1 especially in the configuration of the retractable membrane.

In a variant of this hydraulic fluid charging system, shown in FIG. 3, the introduction site 37 consists of the rounded end of the cap forming the membrane 8. In this particular case, the hydraulic fluid 10 is introduced by means of a syringe provided with a needle, which passes through the said membrane at the site 37.

In one embodiment, shown in FIGS. 1, 2 and 3, the channel 16 for the introduction of hydraulic fluid, in the cylindrical body 1, has, over at least part of its length, a hollow needle 2 which extends, at its tapered point, inside the recess 110 in the said cylindrical body, the said hollow needle 2 being associated in a leaktight manner with the said channel 16 and serving on the one hand to supply the wall 112 of the piston 12 with hydraulic fluid, and to fix the tubular reservoir 13 firmly to the said cylindrical body 1.

In this embodiment, the fixing of the tubular reservoir 13 to the cylindrical body 1 by means of the hollow needle 2 is effected by virtue of a stopper 11 blocking the said reservoir 13 on the opposite side to that of administration, the said stopper, through which the said needle passes in a leaktight manner, being housed, over at least part of its thickness, in the interior of the said reservoir 13 and located upstream of the piston 12, which is capable of sliding in a leaktight manner inside the said reservoir 13, the tapered point of the said needle 2 coming out of the said stopper in the vicinity of the wall 112 of the said piston.

In practice, the stopper 11 is provided with two opposite coaxial recesses 111 and 211 so as to reduce the thickness of material through which the tapered point of the needle 2 has to pass.

As indicated above, the hydraulic accumulator has an elastically retractable membrane 8 which is crimped or fixed in a leaktight manner over at least part of the outer surface 101 of the body 1 by means of at least one ring 9. In practice, the elastically retractable membrane 8 is intended to lie on the greater part of the said surface 101 before the hydraulic fluid is introduced into the space 10a and after the contents of the tubular reservoir 13 have been administered. As illustrated in FIGS. 1, 2 and 6, the membrane 8 can constitute a sleeve secured in a leaktight manner to the wall 101 by two rings 9 and 9', each of which is advantageously located in the vicinity of one end of the cylindrical body 1, or, as shown in FIG. 3, it can constitute a cap also covering the site 37 for introduction of the hydraulic fluid into the system, the said cap being secured in a leaktight manner by a single ring 9 to the surface 101 at the point where it is open to the outside, in the vicinity of the opening in the recess 110 in the body 1.

In practice, the internal diameter of the sleeve according to FIGS. 1, 2 and 6, on the one hand, and of the cap according to FIG. 3, on the other, is preferably less than the external diameter of the cylindrical body 1 under normal conditions. Such an arrangement ensures a substantially uniform pressure over the surface 101 of the body 1 until virtually all the fluid 10 contained in the space 10a has been used to administer the total volume of the medicinal preparation 21.

According to the invention, to ensure that the fluid 10 flows correctly towards the capillary duct 4 when administration is complete, i.e. when the membrane 8 comes into contact with the surface 101, it is recommended to use a surface 101 possessing one or more grooves 314 (see FIG. 3), for example one or more longitudinal grooves or alternatively a groove running in a spiral along the surface 101 and acting as a fluid collector near the inlet of the capillary duct 4.

The membrane 8, which is retractable after having been dilated by the introduction of hydraulic fluid 10 into the space 10a, is selected from materials having a high modulus of elasticity (large elongation at break) and the ability to return to the original dimensions after prolonged elongation. Materials suitable for this purpose are natural rubber or synthetic rubber obtained especially by the vulcanization of natural latex, neoprene or polybutadiene, or alternatively silicone rubber. The rubber obtained from natural latex concentrated by evaporation and self-vulcanizing, especially that known under the tradename REVULTEX® MR. This material has the advantage of being relatively stable on storage, both when empty and under pressure, in the sense that it withstands ageing by oxidation (it effectively contains antioxidants). As its ratio pressure when empty/pressure when charged is very close to the value 1, the rate of administration of the preparation 21, especially by perfusion, will be substantially identical from start to finish. For example, with the material REVULTEX® MR mentioned above, for a device administering 10 ml of medicinal preparation 21, the pressure when empty is approximately 0.6 kg/cm$^2$ and the pressure when charged is approximately 0.65 kg/cm$^2$, i.e. a difference of 8.3%; for a device administering 5 ml of medicinal preparation 21, the pressure when empty is approximately 0.75 kg/cm$^2$ and the pressure when charged is approximately 0.8 kg/cm$^2$, i.e. a difference of 6.6%. The desired pressure when empty is obtained by choosing the thickness of the sleeve or cap, on the one hand, and the permanent elongation of the said sleeve or said cap, on the other. Thus, with the device in FIG. 1, if the thickness of the sleeve made of REVULTEX® MR rubber mentioned above is 1.4 mm, the diameter of the sleeve before assembly is 13.3 mm and the external diameter of the body 1 is 20 mm, the permanent elongation of the sleeve is 150%.

In the device of the invention, the membrane 8 is therefore in the form of a sleeve or cap placed around the cylindrical body 1. According to one of the characteristics of the invention, the diameter of the said sleeve or cap in the unstretched state is less than that of the surface 101 of the said body 1 and the ratio:

$$R = \frac{\text{pressure when charged} - \text{pressure when empty}}{\text{pressure when empty}}$$

of the said membrane 8 placed around the said body 1 is between 0.05 and 0.10 and advantageously between 0.06 and 0.09.

Thus, when the space 10a is devoid of fluid 10, the pressure of the membrane 8 when empty is not zero.

In the space 10a, the hydraulic fluid 10 is confined by the membrane 8, the surface 1 and the capillary duct 4 restraining the flow of the said fluid under the pressure of the said membrane 8 towards the channel 16 and the wall 112 of the piston 12.

According to the invention, the capillary duct 4 has a uniform diameter and is made in a part 44 which can be housed in a leaktight manner in an appropriate recess in the cylindrical body 1, between the hydraulic accumulator and the introduction channel 16.

As the flow is governed by the pressure of the fluid in the space 10a, the viscosity of the hydraulic fluid and the diameter of the capillary, it is important for the diameter of the capillary to be as precise as possible. The required precision is illustrated in Table I below, which gives the variations in capillary cross-section as a function of 1 μm variations in diameter.

TABLE 1

| Variation in capillary diameter | Diameter (μm) | Cross-section (μm$^2$) | Variation in cross-section (%) |
|---|---|---|---|
| 10 μm ± 1 μm | 11 | 950 | +21 |
| | 10 | 785 | 0 |
| | 9 | 636 | −19 |
| 40 μm ± 1 μm | 41 | 1320 | +5 |
| | 40 | 1257 | 0 |
| | 39 | 1194 | −5 |
| 80 μm ± 1 μm | 81 | 5152 | +2.6 |
| | 80 | 5020 | 0 |
| | 79 | 4901 | −2.4 |

The diameter of the capillary duct 4 according to the invention has a tolerance of less than 1 μm. The duct 4 can be made in several ways. In one method, the duct 4 is drilled in a quartz part 44 according to the required diameter, with a precision of less than 1 μm, for example using a monocrystalline piece of quartz. In another method according to the invention, the duct 4 is made by providing a drawn wire 404 having a diameter determined to within ±1 μm as shown in FIG. 8, wire 404 is stretched between elements represented by 402 and 403. The wire 404 is arranged along the axis of a mold 400 of frustoconical shape, whose lower, i.e. smaller, cross-section is blocked with an appropriate part 401. A constant volume of a low-melting alloy, for example WOOD's alloy (which melts at 70° C.) or DARCET's alloy (which melts at 100° C.), or alternatively a plastic, especially one which can be crosslinked by means of an appropriate substance or catalyst, is poured into the cavity 44 of this mold. After solidification, it suffices to remove the wire 404, which is generally made of steel. The high-precision capillary duct according to the invention is demolded and is ready to be fitted.

In practice, the cavity 44 can have a height of between 0.5 and 20 mm and, if appropriate, a conicity of the order of 2% to 10%, it being possible for the lower diameter of the said cavity to be of the order of 2 mm. As indicated above, the internal diameter of the capillary duct 4 is between 10 and 900 μm.

The tubular reservoir 13, which is of cylindrical shape; has a narrowing of the LUER cone type at one of its ends and is integral with the cylindrical body 1, its contents 21 being driven either directly or indirectly by the partition 112a of the piston 12 at its other end.

In one embodiment according to the invention, the interior of the tubular reservoir 13 can contain the piston 12. In other words, the said the piston 12 located inside the recess 110 in the cylindrical body 1 is designed so as to be capable of sliding inside the reservoir 13 containing the medicinal preparation 21.

As indicated above, the hollow needle 2 acts in this embodiment as a support for the tubular reservoir 13 via the stopper 11 and as a means of introducing hydraulic fluid onto the face 112 of piston 12.

In another embodiment, as illustrated in FIG. 6 the tubular reservoir 13 is integral with the body 1 via a fixing system comprising a flange 61 provided at the end of the body 1 in the region of the opening in the recess 110, at least one rod 60, 60a associated with the said flange 61, and a means 62 of the vice type, locking the rod 60 and/or the rod 60a via an appropriate element, for example a screw 63. In this embodiment, the piston 12 located inside the recess 110 in the cylindrical body 1 is designed so as to drive, by means of the pressure of the hydraulic fluid on its wall 112, a thrust system 121, 221 acting on the contents of the reservoir 13, the said thrust system being integral with the said reservoir 13, capable of sliding inside the said reservoir 13 and housed at least partially inside the said recess 110.

Figure 4:
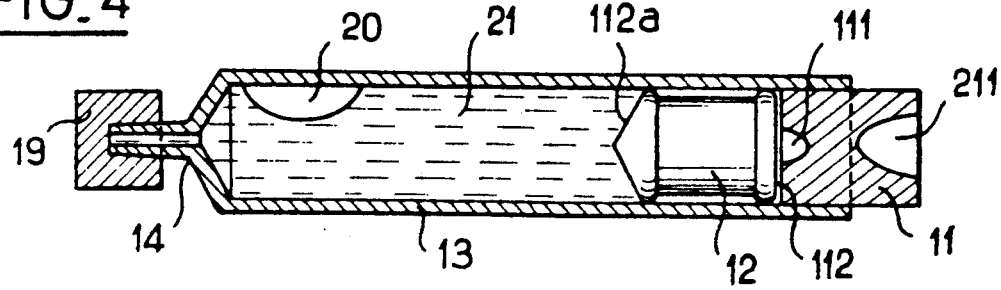

FIGS. 4 and 5 illustrate the modalities to be followed prior to fixing the tubular reservoir 13 by means of the needle 2 as shown in FIG. 1 and 3. When the medicinal preparation 21 is stored in the reservoir 13, the latter is blocked by a stopper 19 placed on the LUER cone at one of its ends, on the one hand, and by a stopper 11 in contact with the face 112 of the piston 12 housed in the said reservoir, on the other. The said stopper 11 is partially housed in the tube 13, part of the said stopper projecting outside the tube 13. The preparation 21 contained in the said reservoir has a meniscus or bubble 20 (see FIG. 4).

Before the device is brought into service, the tubular reservoir 13, prefilled with the preparation 21, is manipulated, in the vertical position, to remove the stopper 19 from the LUER cone. The stopper 11 is pushed in by exerting a force in the direction of the arrow 23, the penetration of the said stopper 11 inside the reservoir 13 driving the bubble 20 out through the LUER cone and raising the piston 12 in the direction of the arrow 22 (see FIG. 5). The reservoir 13 is then placed in the recess 110 so that the needle 2 pierces the stopper 11 and holds the said reservoir in place in the said body.

This procedure makes it possible to overcome the disadvantage, which can arise fairly frequently, of adhesion of the piston 12 to the tubular reservoir 13 during storage. Pushing along the arrow 23 makes it possible to eliminate the said adhesion. According to this procedure, when the reservoir 13 is held by the stopper 11 perforated by the hollow needle 2, the outer wall of the said reservoir can be at a distance from the wall 214 of the recess 110.

The device shown in FIG. 6 is designed as an automatic syringe. More precisely, the reservoir 13 is fitted into a syringe, the medicinal preparation 21 contained in the said reservoir being driven by the pressure of the hydraulic fluid exerted on the wall 112 of the piston 12 (the wall 112a moving from position X to position Y in order to distribute the preparation 21) and transmitted via a plunger 121 actuated by the wall 112a of the said piston 12. Here the wall 112a of the piston 12 acts on the upstream plate 122 of the plunger 121, and the plate 122a of the plunger acts on the upstream face 222 of the piston 221 housed in the tubular reservoir 13.

In this variant, the said plunger 121 drives a piston 221 capable of sliding inside the reservoir 13, the said reservoir being integral with the said cylindrical body 1 via a fixing system, represented schematically by the elements 60, 62 and 63, joined to the outside opening in the recess 110 of (sic) the flange 61 of the said cylindrical body 1.

According to another characteristic of the invention, the administration device is such that the hydraulic fluid 10 can be recycled. The device shown in FIG. 6 has a recycling system of the type comprising a ball 70 secured to an appropriate spring 72, both of which are housed in a recess 71 in the cylindrical body 1. When administration takes place, the ball 70, under the action of the spring 72, blocks the channel 73 communicating with the bottom 210 of the recess 110. When recycling is effected and the piston 12 is pushed back by an appropriate means, especially a rod (not shown here), the ball 70, driven by a pressure greater than that of the spring 72, frees the outlet of the channel 73 in order to allow the hydraulic fluid 10 to pass into the cavity 17 via the tube 74 and then into the space 10a via the slot 18.

In another preferred embodiment of the invention, the face 112 of the piston 12 is grooved or ribbed so as to improve the driving of the piston 12 by the fluid 10.

As illustrated in FIG. 6, the wall 112 of the piston 12 can have a surface homologous to that of the bottom 210 of the recess 110.

The device according to the invention can be used for the administration of a medicinal preparation by perfusion, the mode of administration being intravenous, intraarterial, intramuscular, intradermal or subcutaneous. Good results have been obtained with the device in FIG. 1 using intradermal perfusion. For perfusion, the LUER cone 14 is connected to the patient's catheter by a flexible tube.

The device in FIG. 1 can also be used for percutaneous administration, as shown in FIG. 7, where a tube 150 of small diameter joins the LUER cone to a porous material 151 placed on top of the skin 153 and attached thereto via an appropriate fixing means 152, especially of the type comprising at least one adhesive compound and at least one protective film, which can be microperforated. The porous material 151, which is in the form of a plate or disk of large dimensions compared with its thickness, allows the active principle or principles to pass through the skin by a mechanism well known to those skilled in the art (large area and small thickness of porous material soaking the region of skin involved in the administration).

The device according to the invention, especially the one shown in FIG. 1 and more particularly in FIG. 3, can be used for administration via the abdomen (in particular by intraabdominal implantation), the rectum (especially by perfusion) or the scrotum (especially by perfusion or percutaneously).

In practice, the total volume of hydraulic fluid 10 to be introduced into the device of the invention is substantially equal to or slightly greater than the volume of medicinal preparation 21 to be administered in accordance with the embodiments shown in FIGS. 1 and 3.

In the case of the embodiment in FIG. 6, provision can be made, if appropriate, for the total volume of hydraulic fluid to be considerably greater than that of the volume (sic) of the preparation 21 to be administered.

When it is used for administration by perfusion, the device according to the invention has sufficiently small dimensions that it can be carried in the pocket of a garment or as a pendant around the neck, or places (sic) near the introduction site in the case of transrectal or transscrotal administration.

The device according to the invention can be supplied in a variety of sizes for a single administration (disposable device) or for multiple administration (device with recycling of the hydraulic fluid).

What is claimed is:

1. A method for the administration of a liquid medicinal preparation comprising the steps of:
   (a) providing a device for the continuous administration of a liquid medicinal preparation, said device having a body and a reservoir disposed in the body, and an elastic membrane surrounding at least a portion of the body;
   (b) dilating the membrane by inserting fluid into the membrane;
   (c) placing a medicinal preparation in said reservoir;
   (d) forcing the fluid through a capillary duct and onto a moving wall disposed in said reservoir by retracting the elastic membrane to administer the medicinal preparation from the reservoir.

2. The method according to claim 1, wherein the flow of the medicinal preparation to be administered is regulated by the diameter of the capillary duct (4) and the viscosity of the hydraulic fluid.

3. The method according to claim 1 or claim 2, wherein the hydraulic fluid (10) can be recycled.

4. The method according to claim 1 or claim 2, wherein the hydraulic fluid (10) is selected from the group consisting of liquid media, especially water, saline solutions, oils, polyalkylene glycols, silicones and mixtures thereof.

5. The method according to claim 1 or claim 2, wherein the total volume of hydraulic fluid to be introduced is substantially equal to or slightly greater than the volume of medicinal preparation to be administered.

6. A device for the continuous administration of a liquid medicinal preparation, comprising:
   (a) a cylindrical body having a recess hollowed out of the cylindrical body and open to the outside, the recess running along a longitudinal axis of the cylindrical body;
   (b) a reservoir having an administration site, the reservoir being disposed in the recess;
   (c) a retractable elastic membrane being fixed in a lock-tight manner to at least a portion of an outer surface of the cylindrical body;
   (d) a hydraulic accumulator which is driven by the elastic membrane and which comprises a hydraulic fluid which can be accommodated in a space, the space being situated between the elastic membrane which has been dilated by insertion of the fluid and an outer surface of the cylindrical body;
   (e) a capillary duct connected to the accumulator and supplied with the fluid by the accumulator;
   (f) a piston located downstream of the capillary duct and driven by the fluid coming from the capillary duct, the piston providing for a continuous transfer of the medicinal preparation contained in the reservoir through the administration site.

7. The device according to claim 6, further comprising:
   a channel located in a bottom of the recess, the channel being supplied with the hydraulic fluid from the capillary duct, wherein said piston is situated in the recess, the piston being capable of moving axially inside the recess, the piston further comprising a first face driven by the fluid coming from the channel and a second face which provides for a continuous transfer of the medicinal preparation through the administration site, and wherein the reservoir is tubular.

8. The device according to claim 7; wherein the piston is capable of sliding inside the reservoir.

9. The device according to claim 7, wherein the reservoir has an integral thrust system, the thrust system being capable of sliding inside the reservoir and being at least partially housed inside the recess, the thrust system being driven by a pressure from the hydraulic fluid which is exerted on the first face of the piston.

10. The device according to claim 9, wherein the reservoir is disposed in a syringe, the medicinal preparation being driven by the pressure of the hydraulic fluid exerted on the first face of the piston, said pressure being transmitted via a plunger actuated by the second face of the piston.

11. The device according to claim 10, further comprising:
   a second piston capable of sliding inside the reservoir, the second piston being driven by the plunger;
   a fixing system joined to the outside opening of the recess, the fixing system integrally connecting the reservoir to the cylindrical body.

12. The device according to claim 7, further comprising a hollow needle which extends over at least a part of the channel in a lock-tight manner, the needle having a taper at one end which extends inside the recess, the needle supplying the first face of the piston with hydraulic fluid and also fixedly connecting the reservoir to the cylindrical body.

13. The device according to claim 12, further comprising a stopper fixedly connecting the needle to the cylindrical body, the stopper blocking the reservoir on a side opposite the administration site, the needle passing through the stopper in a lock-tight manner, the stopper being housed over at least a portion of its thickness in the interior of the reservoir and located upstream of the piston, wherein the piston is capable of sliding in a locktight manner inside the reservoir and wherein the tapered point of the needle extends through the stopper proximate the first face of the piston.

14. The device according to claim 7 further comprising a part within which the capillary duct is made, the duct having a uniform diameter, the part being located in a lock-tight manner in a second recess in the cylindrical body, the second recess being located between the accumulator and the channel.

15. The device according to claim 7, wherein at least a second recess which is open to the outside is formed in said cylindrical body, the second recess being opposite the longitudinal recess, and further comprising means for charging the hydraulic accumulator, the means for charging being housed within the second recess.

16. The device according to claim 6 or claim 19, wherein the elastic membrane is constructed in the form of one of a sleeve and a cap placed around the cylindrical body, the diameter of the sleeve in an unstretched state being less than that of a diameter of the outer surface of the cylindrical body and a ratio R:

$$R = \frac{\text{pressure when charged} - \text{pressure when empty}}{\text{pressure when empty}}$$

of the membrane being between 0.05 and 0.10.

17. The device according to claim 6 or claim 19, wherein the elastic membrane is constructed in the form of one of a cap and a sleeve placed around the cylindrical body, the diameter of the cap in an unstretched state being less than that of a diameter of the outer surface of the cylindrical body and a ratio R:

$$R = \frac{\text{pressure when charged} - \text{pressure when empty}}{\text{pressure when empty}}$$

of the membrane being between 0.06 and 0.09.

18. A method according to claim 1, further comprising the step of forcing the fluid into and through a duct by retracting the membrane, thereby controlling the flow of fluid into the moving wall.

* * * * *